United States Patent [19]

Weiss

[11] Patent Number: 5,179,946
[45] Date of Patent: Jan. 19, 1993

[54] APPARATUS AND METHOD FOR ARRHYTHMIA DETECTION BY VARIATIONS IN THE TRANSCARDIAC IMPEDANCE BETWEEN DEFIBRILLATION PATCHES

[75] Inventor: Steven M. Weiss, West Plymble, Australia

[73] Assignee: Telectronics Pacing Systems, Inc., Englewood, Colo.

[21] Appl. No.: 617,987

[22] Filed: Nov. 26, 1990

[30] Foreign Application Priority Data

Dec. 28, 1989 [AU] Australia .............................. PJ 8038

[51] Int. Cl.⁵ ......................... A61N 1/39; A61N 1/368
[52] U.S. Cl. ......................... 128/419 D; 128/419 PG; 128/734
[58] Field of Search .................. 128/419 D, 734, 723, 128/670, 671, 419 PG

[56] References Cited

U.S. PATENT DOCUMENTS

| 4,030,509 | 6/1977 | Heilman et al. | 128/419 D |
| 4,291,699 | 9/1981 | Geddes et al. | 128/419 D |
| 4,303,075 | 12/1981 | Heilman et al. | 128/419 PG |
| 4,562,843 | 1/1986 | Djordjevich et al. | 128/672 |
| 4,596,251 | 6/1986 | Plicchi et al. | 128/723 |
| 4,686,987 | 8/1987 | Salo et al. | 128/419 PG |
| 4,702,253 | 10/1987 | Nappholz et al. | 128/419 PG |
| 4,730,619 | 3/1988 | Koning et al. | 128/419 PG |
| 4,733,667 | 3/1988 | Olive et al. | 128/419 PG |
| 4,830,006 | 5/1989 | Haluska et al. | 128/419 PG |
| 4,840,177 | 6/1989 | Charbonnier et al. | 128/419 D |
| 4,895,151 | 1/1990 | Grevis et al. | 128/419 PG |
| 4,940,054 | 7/1990 | Grevis et al. | 128/419 PG |

OTHER PUBLICATIONS

"Effects of Atrial and Ventricular Tachycardias on the Cardiovascular Dynamics", Nakano. Jr., Am. J. of Phys. vol. 206, pp. 547-552 (1964).

"Linear AC Electrode Polarization Impedance at Smooth Noble Metal Interfaces", Derosa et al., IEEE Trans. Biomedical Eng., vol. BME 24, No. 3, May 1977.

Primary Examiner—William E. Kamm
Assistant Examiner—Kennedy J. Schaetzle
Attorney, Agent, or Firm—Gottlieb, Rackman & Reisman

[57] ABSTRACT

An implantable device for the treatment of malfunctions of a patient's heart is disclosed. The device employs defibrillation patch electrodes positioned on the outer surface of the heart generally outwardly of the left and right ventricles of the heart, in conjunction with a non-polarizing sub-threshold constant current or constant voltage signal and appropriate electronic signal sensing and processing circuitry, to determine changes in variations of the transcardiac impedance of a patient's heart, such changes being representative of corresponding changes in the level of haemodynamic compromise of the heart. Bradycardia support pacing therapy, antitachycardia pacing therapy, cardioversion therapy and defibrillation therapy, or no therapy, are selectively initiated by the device, depending on the level of haemodynamic compromise determined to be extent by the device. Conventional electrical function sensing may be employed in conjunction with the sensed changes in variations of the transcardiac impedance to control the device. Corresponding methods of treating malfunctions of a patient's heart are also disclosed.

32 Claims, 10 Drawing Sheets

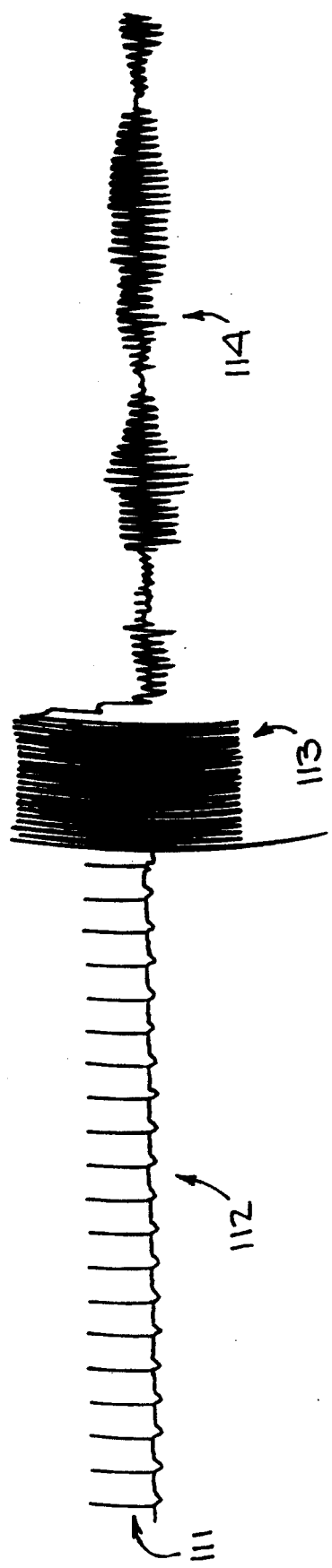
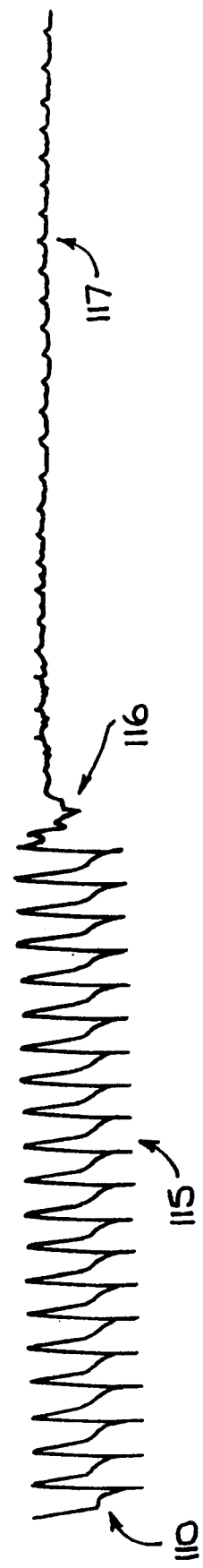
Fig. 6B.
Fig. 6A.

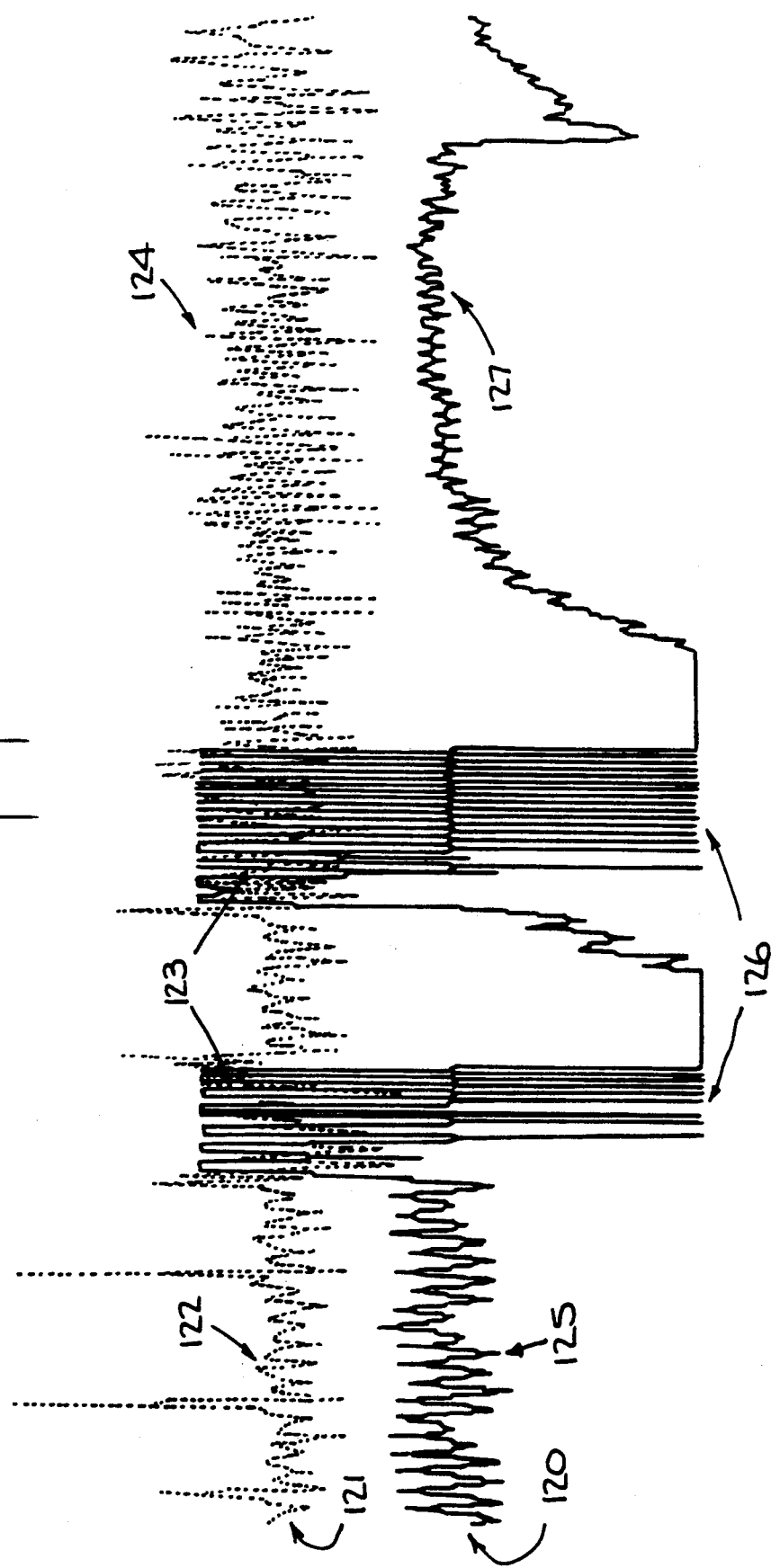

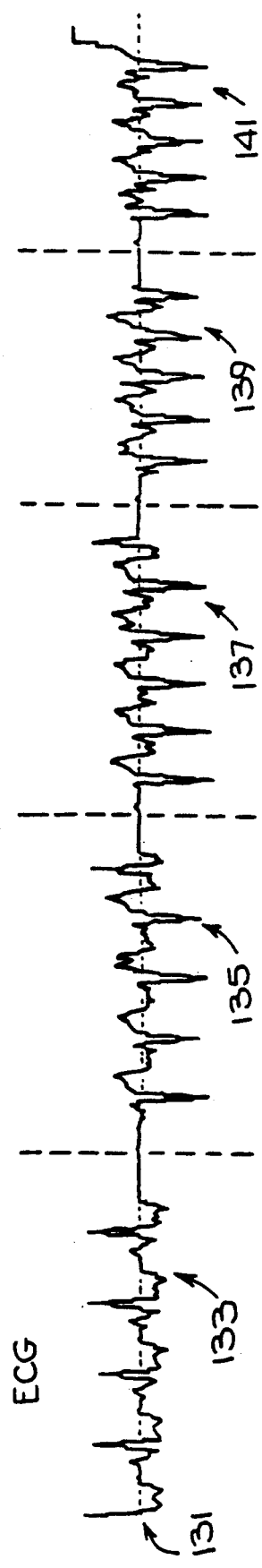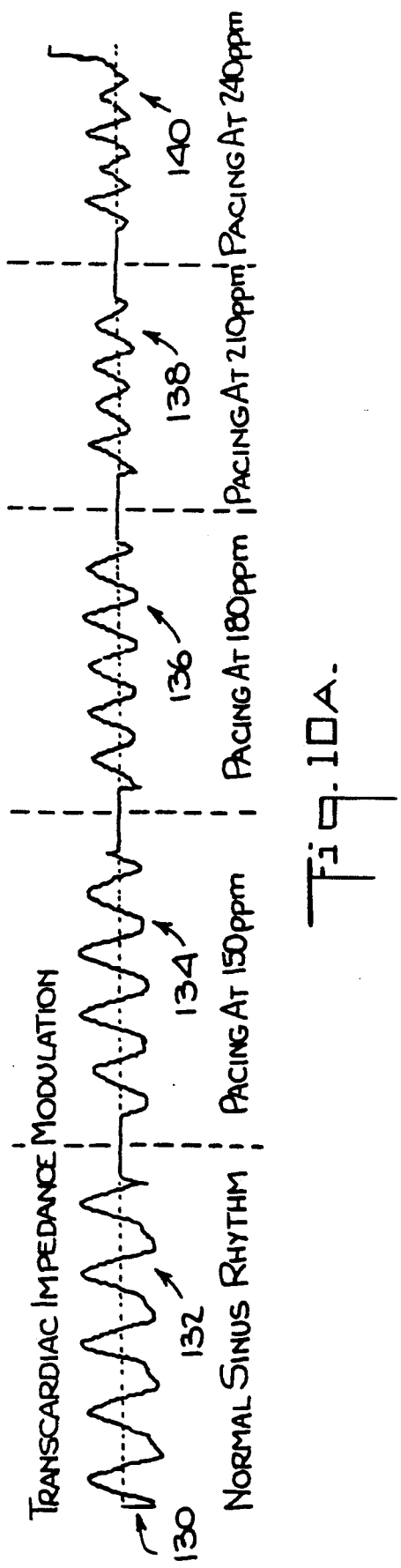
Fig. 10B.
Fig. 10A.

APPARATUS AND METHOD FOR ARRHYTHMIA DETECTION BY VARIATIONS IN THE TRANSCARDIAC IMPEDANCE BETWEEN DEFIBRILLATION PATCHES

BACKGROUND OF THE INVENTION

This invention relates to an implantable cardioverting/defibrillating pacemaker and, more particularly, to a pacemaker of this type which has the ability to sense haemodynamic compromise in a patient's heart. This ability, when incorporated into an automatic implantable arrhythmia control system, is used for the determination of tachyarrhythmias and acts as a trigger for the automatic delivery of antitachycardia pacing, cardioversion and/or defibrillation therapy.

Pacemakers were initially developed to electrically stimulate hearts that were unable to beat at a rate sufficient to maintain a life sustaining cardiac output. The first devices delivered electrical stimuli at a fixed rate, regardless of the heart's function or the body's physiological needs.

Devices were then developed that stimulated the heart only if it failed to beat above a predetermined rate. Such devices sensed the electrical activity of the heart, usually in the right ventricle. Later developments saw the introduction of pacemakers that sensed and stimulated in both the right atrium and right ventricle.

Pacemakers with the ability to sense the physiological demand for an increase in heart rate were then introduced. One example of this is disclosed in U.S. Pat. No. 4,702,253, to Nappholz et al., wherein the device determines physiological demand by the sensing of respiratory minute volume, and increases the pacing rate in response to increases in minute volume.

Devices were developed that electrically sensed the presence of a ventricular tachyarrhythmia and delivered a defibrillating DC shock to revert the heart to a normal rhythm. More advanced devices where developed that paced hearts undergoing a tachyarrhythmia back into normal rhythm.

Recent technology has brought about the development of automatic implantable arrhythmia control systems. These devices are able to pace a heart that is beating too slowly, to cardiovert/defibrillate a fast tachyarrhythmia and to pace a heart undergoing a slower tachyarrhythmia back into a normal rhythm. One such device is disclosed in the U.S. Pat. No. 4,940,054 of Grevis et al. The Grevis et al. device comprises a microprocessor-based arrhythmia control system. It has the capability of being reprogrammed, while implanted, via an external programmer and a radio frequency telemetry link. The use of a telemetric link allows not only the reprogramming of the device but also the interrogation of the device by a clinician. Various parameters, such as bradycardia pacing rate and amplitude, antitachycardia pacing algorithms and cardioversion and defibrillation energies, can be re-programmed to suit the needs of the recipient of the device.

There are limitations inherent in devices of the above type as they rely solely upon the sensing of the electrical activity of the heart as the means of determining the state of cardiac function. Also, there is a possibility that the device may be confused by electrical noise induced in the sensing circuits and causing difficulty in distinguishing a supraventricular tachyarrhythmia (SVT) from a ventricular tachyarrhythmia (VT). Furthermore, although having the ability to detect tachyarrhythmias, such devices are unable to determine whether or not the detected tachyarrhythmia is haemodynamically compromising, regardless of its origin.

It has been shown that there are differences in the haemodynamic effects of the different tachyarrhythmias. This has been documented by Nakano in his article "Effects of Atrial and Ventricular Tachycardias on the Cardiovascular System", Am. J. Physiol., Vol. 206, pages 547-552 (1964). Hence, the application of certain selected therapies may be haemodynamically inappropriate. An example of such a shortcoming is that a patient suffering from a haemodynamically compromising slow VT may be subject to the inappropriate delivery of antitachycardia pacing therapy (ATP), instead of defibrillation therapy. Conversely, a VT may not necessarily be haemodynamically compromising and therefore not require ATP therapy, yet ATP therapy may automatically be delivered by the device.

U.S. Pat. No. 4,730,619, to Koning et al., discloses that the impedance between the ring and tip electrodes of an implantable cardiac pacing lead can be used as measure of cardiac output. This patent uses that measure of cardiac output to optimize the function of a bradycardia support pacemaker. The Koning et al. device is limited in that its application is only for bradycardia support pacing. There is no means disclosed for antitachycardia pacing or cardioversion/defibrillation, nor any method to detect the onset or presence of haemodynamically compromising arrhythmias. Also, the means of sensing the impedance is restricted to the use of the ring and tip electrodes of a bipolar implantable cardiac pacing lead.

U.S. Pat. No. 4,733,667, to Olive et al., discloses a method for closed loop control of cardiac stimulating utilizing rate of change of impedance. Olive et al. use a fixed quadripolar electrode to derive an intracardiac impedance signal to drive a rate responsive bradycardia support pacemaker. Their device is not capable of delivering antitachycardia pacing, nor defibrillation therapy, nor was it designed to recognize haemodynamically compromising arrhythmias.

U.S. Pat. No. 4,702,253, to Nappholz et al., discloses a pacemaker and method of using the same to determine minute volume. In this device the transthoracic impedance is measured and used as a means of determining the respiratory minute volume. It senses the transthoracic impedance between its case and the tip electrode of the ventricular lead. The injected current is passed between the ring electrode of the ventricular lead and the case. Filtering is used to specifically remove the changes in impedance due to the action of the heart. This device is a rate responsive bradycardia support device that specifically filters out the cardiac impedance signal. The patent does not disclose a method to detect haemodynamically compromising arrhythmias, nor the means for delivering antitachycardia pacing nor defibrillation therapy.

U.S. Pat. No. 4,291,699, to Geddes et al., discloses a method and apparatus for automatically detecting and treating ventricular fibrillation. Geddes et al. use the intracardiac impedance sensed between two electrodes mounted upon a permanently implanted intracardiac catheter as a means of confirming the presence of ventricular fibrillation (VF). In the Geddes et al. device the endocardial lead is placed in only one ventricle. It is therefore limited in that it at best accounts for only a part of the volume changes and hence only a portion of the mechanical pumping activity of one ventricle. It also fails to determine the mechanical pumping activity of the other ventricle, and as such is not an accurate measure of haemodynamic compromise. Examples of this shortcoming are when a patient's AV valve fails to close completely, or when there exists the condition of high vascular resistance in the lungs. It is believed that as a result of this there is a large weighting of the electrical aspect of detection.

Our research has shown that the Geddes et al. system is very subject to the positioning of the electrode, especially the tip of the electrode. The endocardial surface of the human ventricle is corrugated. The endocardial rugae and valvular tendineae provide multiple locations in which an electrode may lodge. However, the positioning of an electrode tip within such a corrugation can lead to errors in the measurement of impedance.

The human cardiac tissue has a relatively similar impedance to that of blood. Therefore, changes in blood volume to both of the ventricles of the heart form a large part of the overall impedance between patch electrodes, allowing for blood volume changes to be easily measurable.

If the electrode tip as disclosed in Geddes et al. is sited in a deep rugae, that is, in what is effectively a "well" within the surface of the endocardium, the proportional blood volume changes and hence impedance changes would be considerably lower and therefore more difficult to measure. Also it would be more difficult to accurately measure smaller amounts of impedance changes relating to the higher levels of haemodynamic compromise, as in VT/VF.

The performance of devices that sample intracardiac impedance signals has proven to be subject-variable, with some electrode configurations working in one subject but not in another. In the device of Geddes et al., therapy decisions are made upon the weighted ANDing of right ventricular impedance and rate criteria, with the facility to ignore the impedance signal if its use proves problematic. It has been found by the present inventor that the means of overcoming this problem is to measure the required impedance signal across both the left and right ventricles of the heart. An added feature of my invention is to perform the impedance measurements from the outside of the heart.

Accordingly, it is a primary object of the present invention to provide a device capable of measuring haemodynamic compromise in both ventricles of the patient's heart by determining the changes in normal variations of the transcardiac impedance between defibrillator patches placed on the outer surface of the patient's heart.

An additional object of the invention is to provide a device capable of classifying and detecting tachyarrhythmias according to discrete levels of haemodynamic compromise sensed by the device.

Yet another object of the invention is to provide a safe reliable device capable of delivering appropriate antitachyarrhythmia therapy according to the discrete level of haemodynamic compromise sensed by the device.

Further objects and advantages of the invention will become apparent as the following description proceeds.

SUMMARY OF THE INVENTION

It has been found that haemodynamic compromise can be determined by measuring the amount of change in the normal variations of electrical impedance across both ventricles of the heart. Though the impedance of blood is similar to that of the human heart muscle, the volume of blood within the two ventricles cyclically decreases and increases with contractions and relaxation of the ventricles. Thus, by placing electrodes across both ventricles of the heart, the overall quantity of blood and muscle between these electrodes changes not only cyclically but also in proportion to the amount of blood filling and emptying from the ventricles.

The associated electrical impedance to current flow between the electrodes then changes in response to the filling and emptying of the ventricles with blood. Moreover, the amount of impedance change is related to the amount of filling and emptying of the ventricles, which in turn is related to the performance of the ventricles, and hence the amount of impedance change can be used as an indicator of haemodynamic compromise.

Since the amount of electrical impedance change measured between two electrodes on either ventricle reflects the amount of haemodynamic compromise, the system of the present invention can be used for the determination of an appropriate therapy to be delivered to a patient via an arrhythmia control system, based on the fact that different arrhythmias exhibit different levels of haemodynamic compromise.

A reduction in the magnitude of the changes of electrical impedance across both ventricles of the heart reflects haemodynamic compromise. Furthermore, the amount of reduction in the magnitude of the electrical impedance changes reflects the amount of haemodynamic compromise. This is important since different levels of haemodynamic compromise dictate the appropriate therapy to be delivered by an arrhythmia control system.

The technique of electrical impedance sampling is well known (See, e.g., Webster J. G., "Encyclopedia of Medical Devices and Instrumentation", published by John Wiley and Sons, New York, 1988); it is simply an implementation of Ohm's law (voltage equals current times impedance). The value of the heart and blood impedance changes can be obtained by either applying a constant current source to pass through the tissue and blood and then recording the voltage changes occurring as a result of the cyclic impedance changes, or by applying a constant voltage source and then recording the changing current. The present invention covers both techniques.

Apart from measuring impedance by either a constant current or constant voltage method, consideration needs to be given to the electrode/ventricle interface. It has been shown by De Rosa et al., in an article entitled "Linear AC Electrode Polarization Impedance at Smooth Noble Metal Interface", appearing in IEEE Transactions on Biomedical Engineering, May 24, 1977, Vol. 3, pages 260–268, that the application of a direct current (DC) to implanted electrodes causes polarization at the interface with a corresponding drop in electrode performance. This can be overcome by the use of an alternating current (AC); however, several limitations apply.

With an AC signal, the amplitude becomes modulated by the variations in impedance during the cyclic contraction/relaxation of the ventricles. During analysis of the resultant impedance signal, only the modulations are of concern, and as such, must be filtered out of the combined signal. In addition, care must be taken with the choice of alternating current frequency, as a low frequency can induce a cardiac arrhythmia and a high frequency can induce measurement errors due to capacitive coupling.

An alternative to alternating current is rapid short bursts of charge-balanced current or voltage. This has the added appeal of consuming less energy overall by not applying current or voltage continuously to the electrodes. As the cyclic contractions of the ventricles are comparatively slow (usually around 1-2 cycles per second), a rapidly beating short burst of current or voltage can effectively be considered as being continuous. This signal also needs to be demodulated.

One complication of measuring transcardiac impedance from a pair of electrodes on either ventricle is that large voltages may appear on the electrodes during defibrillation or cardioversion. In particular, if the transcardiac impedance signal is being used in conjunction with an implantable defibrillator or cardioverter, much of the energy required for defibrillation or cardioversion could be shunted through the transcardiac impedance circuit. It is a necessary part of the present invention that the transcardiac impedance circuitry be protected from external transthoracic defibrillation shocks as well as being able to be entirely isolated from the ventricle during delivery of defibrillation or cardioversion therapy from an implantable defibrillator/cardioverter/arrhythmia control system. Such protection also enables the same electrodes as used for defibrillation/cardioversion to be used for transcardiac impedance measurement.

There are several factors that would also affect the impedance that are not related directly to cardiac function. Above all, the transthoracic impedance varies with respiration so that appropriate filtering is needed to remove the effect of the 0.1–0.5 Hz respiratory impedance signal. Artifacts in the transcardiac impedance signal may occur with coughing and very rapid hyperventilation. The transcardiac impedance signal may in some circumstances be not entirely suitable as the only basis of arrhythmia detection when using an implantable arrhythmia control system, and in these cases it is preferable that it be used in conjunction with the electrically sensed heart rate.

A device according to the present invention uses the transcardiac impedance signal, in a reliable and consistent manner, to determine the onset of haemodynamically comprising arrhythmias. It initiates antitachycardia pacing and defibrillation therapy in accordance with the level of haemodynamic compromise that is determined.

SUMMARY OF TERMS

"Haemodynamic Compromise"—exists when there is either insufficient blood pressure or blood flow through both ventricles of the heart to meet the oxygen demands of the tissues of the body. In extreme cases this may produce unconsciousness, and even death. It is a relative term since the amount of oxygen required varies with the level of activity, the level of consciousness, feeding, etc. It is well known that tachyarrhythmias cause a decrease in blood output from the heart and are therefore considered to be haemodynamically compromising.

"ECG Electrocardiograph"—The ECG is, strictly speaking, the graphical representation of the electrical activity of the heart. However, the term ECG is used loosely to refer to the electrical activity of heart. The electrical activity of the heart can be sensed either on the surface of the skin, or on or in the heart.

"VF"—Ventricular Fibrillation.

"VT"—Ventricular Tachycardia.

"Transcardiac Impedance (Z)"—This is the impedance to electrical current flow (I) through the ventricles of the heart, across which there exists a voltage (V). As defined by Ohm's law: $Z = V/I$. Z may be obtained by applying a constant known current, and measuring V, or by applying a constant known voltage, and measuring I.

"Delta Z"—Change of Z as a result of changes to the overall blood volume of both ventricles of the heart.

"Cardioverter/Defibrillator"—is a device that can sense tachyarrhythmias in the heart and deliver an electric charge to the heart in order to revert it back to a normal rhythm. The difference between a cardioverter and a defibrillator lies only in the amount of energy delivered to the heart. Cardioversion is usually used to refer to low energy shocks, and defibrillation to high energy shocks. A cardioverter/defibrillator is usually capable of supplying energies in a range of less than 1 Joule to more than 40 joules. The shocks may or may not be synchronized with the R-wave of the ECG.

"Arrhythmia Control System"—is a device that can perform both cardioverting/defibrillating and pacemaking functions. When referred to herein, it equally applies to devices that deliver their energy synchronously with a detected R-wave, and to devices that do not. When used, the term will usually apply to devices that electrically sense/stimulate via electrodes in the right ventricle and right atrium but could also apply to devices that do so only in the right ventricle, in the right atrium alone, in multiple heart chambers, via epicardial patches or leads, or via other sense/stimulation configurations.

"Antitachycardia Pacing (ATP)"—is a technique implemented in some pacemaking devices. Its aim is to pace a rapidly and abnormally beating heart back into a more normal rhythm. Its use implies that the tachyarrhythmia detected is considered not to be so sufficiently haemodynamically compromising that it will endanger vital organs within the anticipated treatment time. ATP may produce a more malignant tachyarrhythmia; for example, ventricular tachycardia (VT) may be paced into ventricular fibrillation (VF). For this reason, ATP is normally implemented only when there is the option to use cardioversion/defibrillation therapy.

BRIEF DESCRIPTION OF THE DRAWINGS

FIGS. 8A and 8B are respective graphic illustrations of the response of an impedance driver/sense circuit to the induction of ventricular fibrillation and a surface ECG that is shown for comparison purposes;

FIG. 9 shows graphic illustrations of the response of an impedance driver/sense circuit to the induction of ventricular tachycardia and a surface ECG that is shown for comparison purposes; and, FIGS. 10A and 10B are respective graphic illustrations of the response of an impedance driver/sense circuit to a variety of fast pacing rates which are increasingly haemodynamically compromising and a surface ECG that is shown for comparison purposes.

DETAILED DESCRIPTION OF THE INVENTION

Figure 1:
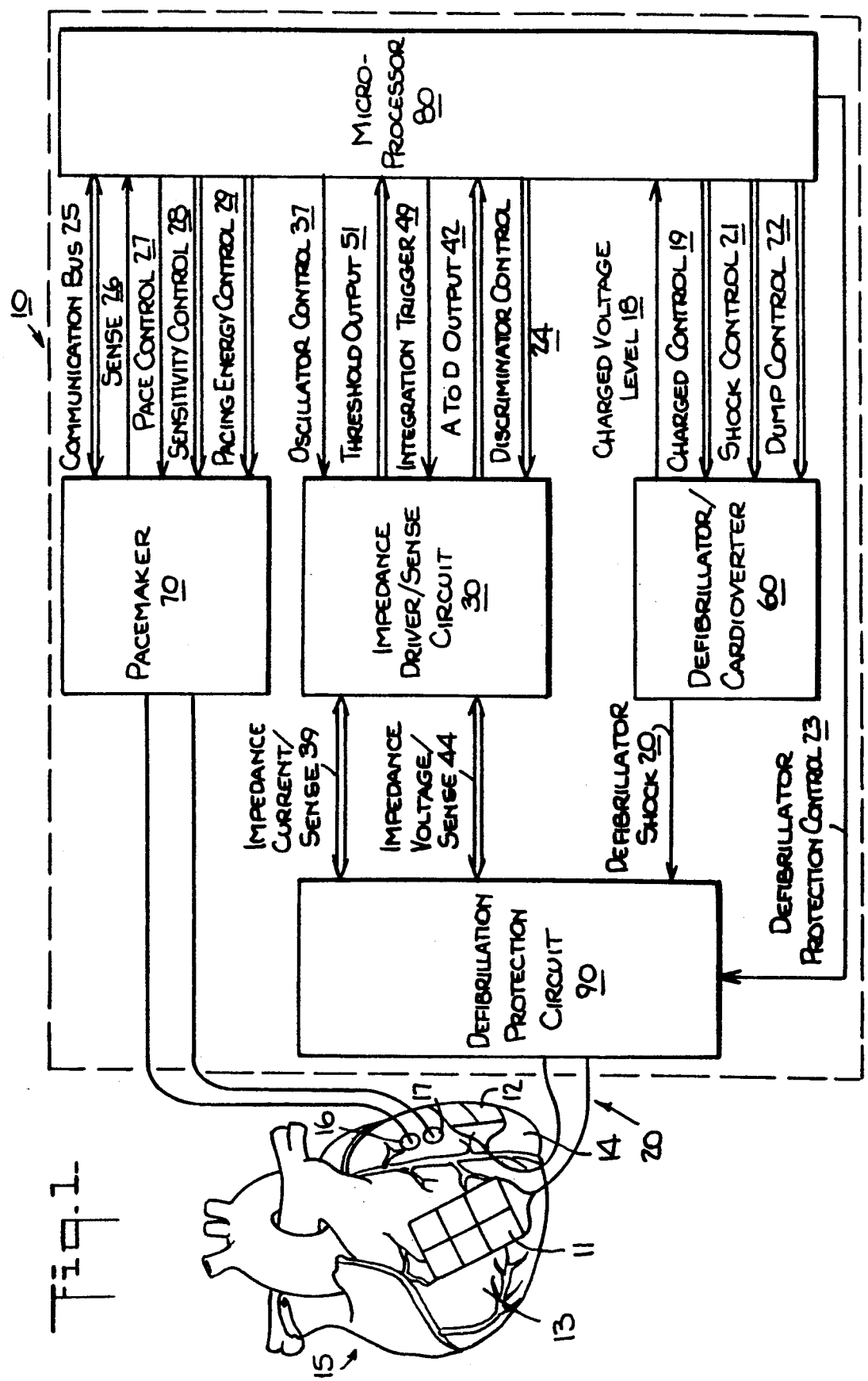
FIG. 1 illustrates a block diagram of an implantable arrhythmia control system in which the present invention is incorporated.

Referring to FIG. 1, there is described a block diagram of an implantable arrhythmia control system or apparatus, shown generally at 10, in which the present invention is incorporated.

A pair of implantable defibrillator patches or electrodes 11 and 12 are shown attached to the outer surface of a patient's heart 15, generally outwardly of the respective right ventricle 13 and left ventricle 14 of the heart. The defibrillator patches 11 and 12 constitute the complete electrode system for an impedance driver/sense circuit, shown generally at 30. The defibrillator patches 11 and 12, used as electrodes for the impedance driver/sense circuit 30, are also used as electrodes for a defibrillator/cardioverter, shown generally at 60, this being an important feature of the present invention.

Figure 2:
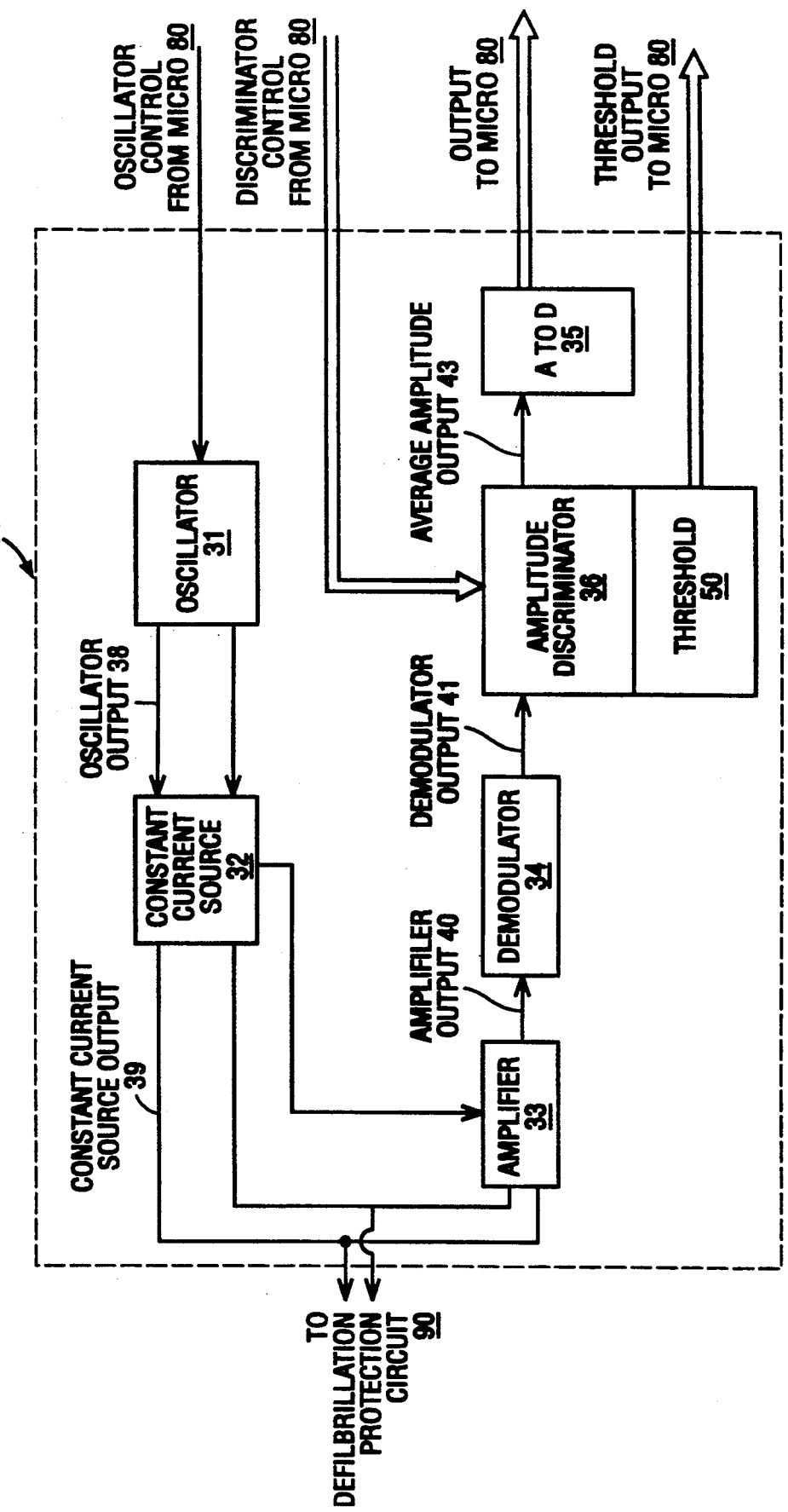
FIG. 2 illustrates a block diagram of a preferred embodiment of an impedance drive/sense circuit utilized in the system of FIG. 1.

There are two basic modes of operation of the impedance driver/sense circuit 30, both of which will be discussed in greater detail hereinafter. Essentially, however, electrical changes to the electrical impedance of the ventricles 13 and 14 of the heart 15 can be determined by either applying a constant amplitude sub-threshold voltage to the defibrillator patches 11 and 12, and measuring changes in the current passing through ventricles 13 and 14 and between the patches 11 and 12 (the embodiment illustrated in FIG. 3); or it can be determined by applying a constant amplitude sub-threshold current to pass between the patches 11 and 12 and through the ventricles 13 and 14, and measuring the voltage changes across the patches 11 and 12 (as illustrated in the embodiment of FIG. 2). The theory of both methods of impedance measure is explained in detail above in the section entitled "Summary of the Invention."

Just as the impedance driver/sense circuit 30 can both stimulate and sense from the same electrodes (patches 11 and 12), a pacemaker, shown generally at 70, senses the intracardiac electrogram from, and causes pacing voltages to go to, an additional pair of electrodes 16 and 17. The impedance driver/sense circuit 30 is protected from damage during defibrillation by a defibrillation protection circuit, shown generally at 90. Sensed signals from both the pacemaker 70 and the impedance driver/sense circuit 30 are passed on to a microprocessor, shown generally at 80, for processing.

The microprocessor 80 controls both the driving and the sensing circuits of the impedance driver/sense circuit 30, the pacing algorithms of the pacemaker 70, and the generation of cardioversion or defibrillation therapy from the defibrillator/cardioverter 60. Microprocessor 80 also controls the defibrillation protection circuit 90 during the delivery of defibrillation or cardioversion therapy. Therapy from the defibrillator/cardioverter 60 is passed through defibrillation protection circuit 90 to the defibrillator patches 11 and 12, and hence to the ventricles 13 and 14 of the heart 15. Details on each of the control lines are discussed hereinafter.

Detection and/or confirmation and/or reconfirmation of either ventricular fibrillation or ventricular tachyarrhythmia is made by the microprocessor 80 by interpreting data from the impedance driver/sense circuit 30 and/or the measure of cycle length by the pacemaker 70, using electrodes 16 and 17 for the detection of the bipolar intracardiac electrogram. In the event of antitachycardia pacing therapy or bradycardia pacing therapy being required, therapy is delivered by the same electrodes 16 and 17.

The mechanism used for detection of the level of haemodynamic compromise by the impedance driver/sense circuit 30 is to generate a non-polarizing sub-threshold signal, and apply that signal to the defibrillator patches 11 and 12. Due to the changing mechanical dimensions of the ventricles 13 and 14 during their cyclic contractions, the electrical impedance to the flow of sub-threshold current between the two defibrillator patches 11 and 12 also varies. This is reflected in the modulation of the amplitude of the driver signal through the impedance driver/sense circuit 30. Different levels of haemodynamic compromise are reflected in the ventricles 13 and 14 by differing amounts of change in their mechanical dimensions, which in turn is reflected in different amplitudes of modulation in the modulated signal. The sense circuitry in the impedance driver/sense circuit 30 determines the signal amplitude modulation level, which is then passed to microprocessor 80 for processing. Processing within the microprocessor 80 determines the type of therapy to be performed by the implantable arrhythmia control system 10. The therapies that the microprocessor 80 can control are bradycardia pacing and antitachycardia pacing from the pacemaker 70, and cardioversion and defibrillation from the defibrillator/cardioverter 60.

As more fully described below, microprocessor 80 and pacemaker 70 are connected by a communication bus 25, a sense line 26, a pace control line 27, a sensitivity control bus 28, and a pacing energy control bus 29. As also more fully described below, microprocessor 80 is connected to defibrillator/cardioverter 60 by a charge voltage level line 18, a charge control bus 19, a shock control bus 21, and a dump control bus 22.

Focusing now on the present invention, FIG. 2 shows the preferred embodiment of the impedance driver/sense circuit 30. An oscillator 31, capable of oscillating at a variety of frequencies and in either a continuous or an intermittent mode, is controlled by an oscillator control signal 37 from microprocessor 80 (FIG. 1). An oscillating output signal 38 from the oscillator 31 is then regulated to have a constant current from the constant current source 32. A constant current output 39 from constant current source 32 is then passed to defibrillation protection circuit 90 (FIG. 1), for further passage to defibrillator patches 11 and 12 (FIG. 1), and also for protection of the impedance driver/sense circuit 30 during defibrillation. The same output 39 from constant current source 32 is also connected to an amplifier 33 for amplification of the low level amplitude modulated signal. Once amplified to a suitable level by amplifier 33, the output signal 40 thereof is demodulated by a demodulator 34, which provides a demodulated signal 41. In addition to demodulating signal 40, the demodulator 34 filters out the DC offset that is due to the resting impedance between patches 11 and 12 (FIG. 1). Hence the demodulated signal 41, represents the change in impedance caused by the change in ventricular volume.

In the preferred embodiment of the impedance driver/sense circuit 30, the demodulated signal 41 is passed on to an amplitude discriminator 36 which performs two functions: 1) to determine the amplitude of each cycle of the demodulated signal and 2) to either average the amplitudes of a predetermined number of cycles, or detect cycle amplitudes crossing predetermined threshold boundaries. An output 51 from a threshold circuit 50 indicates to microprocessor 80 which therapy, if any, is to be performed by the implantable arrhythmia control system 10. This is done by mapping the threshold level signal 51 against appropriate windows stored in a memory 81 (FIG. 6), wherein each window relates to a different therapy.

An average amplitude output 43 from discriminator 36 is passed on to an analog to digital (A/D) converter 35, from which a digital output 42 is passed on to microprocessor 80 (FIG. 1) for the determination of the appropriate therapy, if any, to be performed by the implantable arrhythmia control system 10. The amplitude discriminator 36 and threshold circuit 50 are controlled, in terms of frequency and period of operation, by microprocessor 80 (FIG. 1), along bus 24.

As an alternative to the amplitude discriminator 36 and threshold detector 50, an integrator (not shown) could be incorporated between the demodulator 34 and the A/D converter 35. In such an embodiment, demodulated signal 41 would be integrated to determine electrical energy, which is directly related to haemodynamic status. Thus, changes in the magnitude of the electrical energy output of the integrator would reflect changes in the level of haemodynamic compromise. The number of cardiac cycles over which the integrator would integrate, in addition to the frequency of operation of the integrator for the sampling of the energy signal, would require a control line similar to the discriminator control bus 24 from microprocessor 80. The energy signal from the integrator would be converted to a digital signal 42 by the A/D converter 35, and then passed on to microprocessor 80 (FIG. 1) for the determination of the appropriate therapy, if any, to be performed by the implantable arrhythmia control system 10 (FIG. 1).

Figure 3:
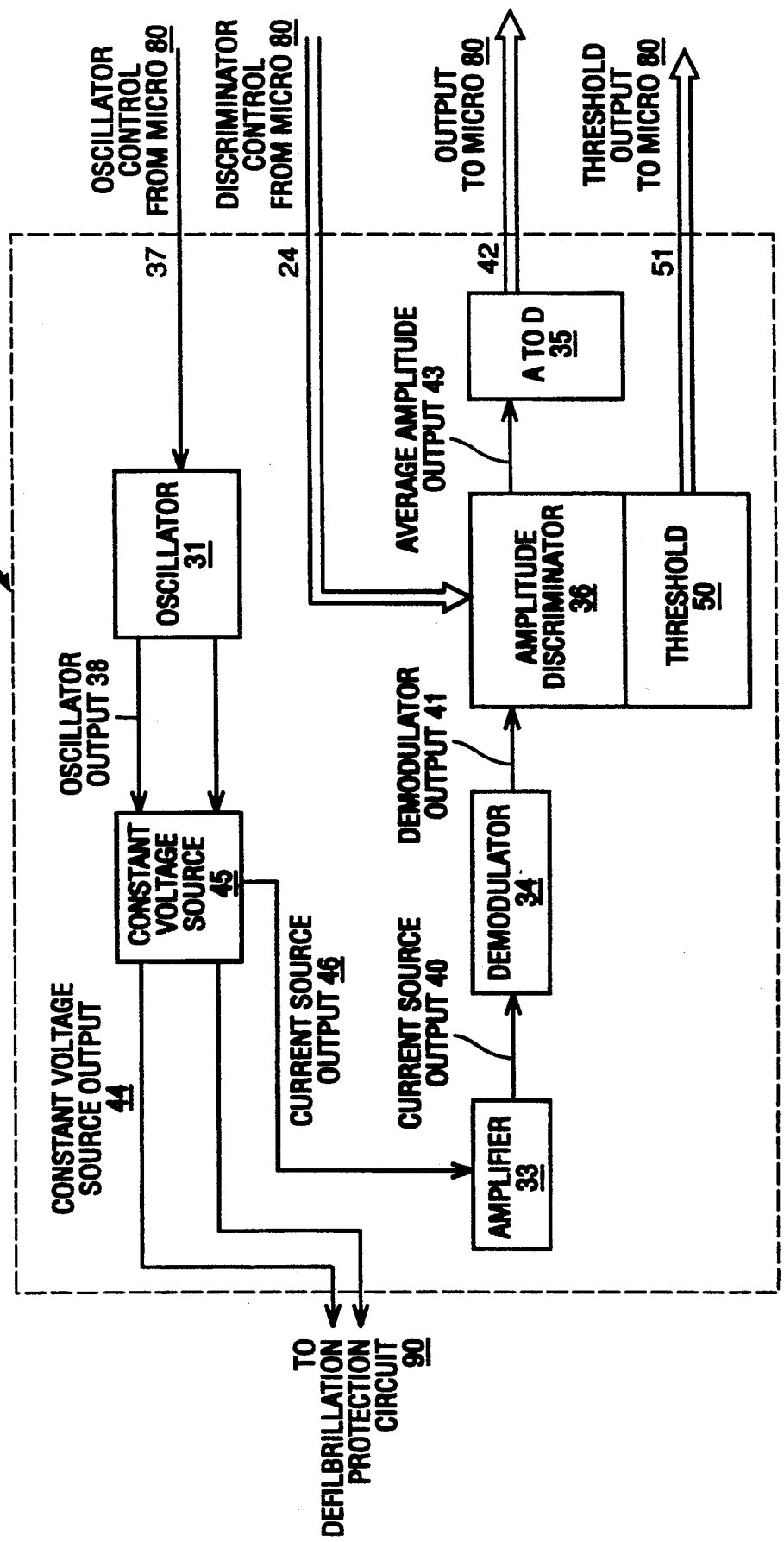
FIG. 3 illustrates a block diagram of an alternative embodiment of an impedance drive/sense circuit that may be utilized in the system of FIG. 1.

Referring now to FIG. 3, an alternative embodiment of the impedance driver/sense circuit 30 is shown. Oscillator 31, which is capable of oscillating in a variety of frequencies and in either a continuous or an intermittent mode, is controlled by signal 37 from the microprocessor 80 (FIG. 1). The oscillating signal 38 from oscillator 31 is then regulated to have a constant voltage amplitude output signal 44 from a constant voltage source 45. The constant voltage output 44 from constant voltage source 45 is then passed to the defibrillation protection circuit 90 (FIG. 1), for further passage to the defibrillator patches 11 and 12 (FIG. 1), and also for protection of the impedance driver/sense circuit 30 during defibrillation or cardioversion.

A current source output 46 from constant voltage source 45 is related to the amount of electrical current being impeded in its flow through the ventricles 13 and 14 (FIG. 1) as produced by the constant voltage source 45 and delivered through the ventricles 13 and 14 (FIG. 1) by means of the patches 11 and 12 (FIG. 1) and the constant voltage source output signal 44. The magnitude of the current source output 46 is modulated by the variations in electrical current flow between patches 11 and 12 (FIG. 1) as a consequence of the changing mechanical dimensions of the ventricles 13 and 14 (FIG. 1) during their cyclic contractions. The current source output 46 is passed to amplifier 33, from where the signal amplitude is amplified and the amplifier output 40 is passed on to demodulator 34. The signal is then demodulated by demodulator 34 to provide a demodulated signal 41. In addition to demodulating signal 40, demodulator 34 filters out the DC offset that is due to the resting impedance between patches 11 and 12 (FIG. 1). Hence, the demodulated signal 41 represents the change in impedance caused by the change in ventricular volume.

In this embodiment of the impedance driver/sense circuit 30, the demodulated signal 41 is passed on to amplitude discriminator 36, which performs two functions: 1) to determine the amplitude of each cycle of the demodulated signal, and 2) to either average the amplitudes of a predetermined number of cycles or detect cycle amplitudes crossing predetermined threshold boundaries. The output 51 from threshold circuit 50 indicates to microprocessor 80 which therapy, if any, is to be performed by the implantable arrhythmia control system 10. This is done by mapping the threshold level 51 against appropriate windows stored in memory 81 (FIG. 6), wherein each window relates to a different therapy.

The average amplitude output 43 from discriminator 36 is passed on to A/D converter 35, from which a digital output 42 is passed on to microprocessor 80 (FIG. 1) for the determination of the appropriate therapy, if any, to be performed by the implantable arrhythmia control system 10. The amplitude discriminator 36 and threshold circuit 50 are controlled, in terms of frequency and period of operation, by microprocessor 80 (FIG. 1) along bus 24.

As an alternative to the amplitude discriminator 36 / threshold detector 50, an integrator (not shown) could be incorporated between the demodulator 34 and the A/D converter 35. In such an embodiment, signal 41 would be integrated to determine electrical energy, which is directly related to haemodynamic status. Thus, changes in the magnitude of the electrical energy output of the integrator would reflect changes in the level of haemodynamic compromise. The number of cardiac cycles over which the integrator would integrate, in addition to the frequency of operation of the integrator for the sampling of the energy signal, would require a control line similar to the discriminator control bus 24 from microprocessor 80. The energy signal from the integrator would be converted to a digital signal 42 by the A/D converter 35, and would then be passed on to microprocessor 80 (FIG. 1) for the determination of the appropriate therapy, if any, to be performed by the implantable arrhythmia control system 10 (FIG. 1).

Figure 4:
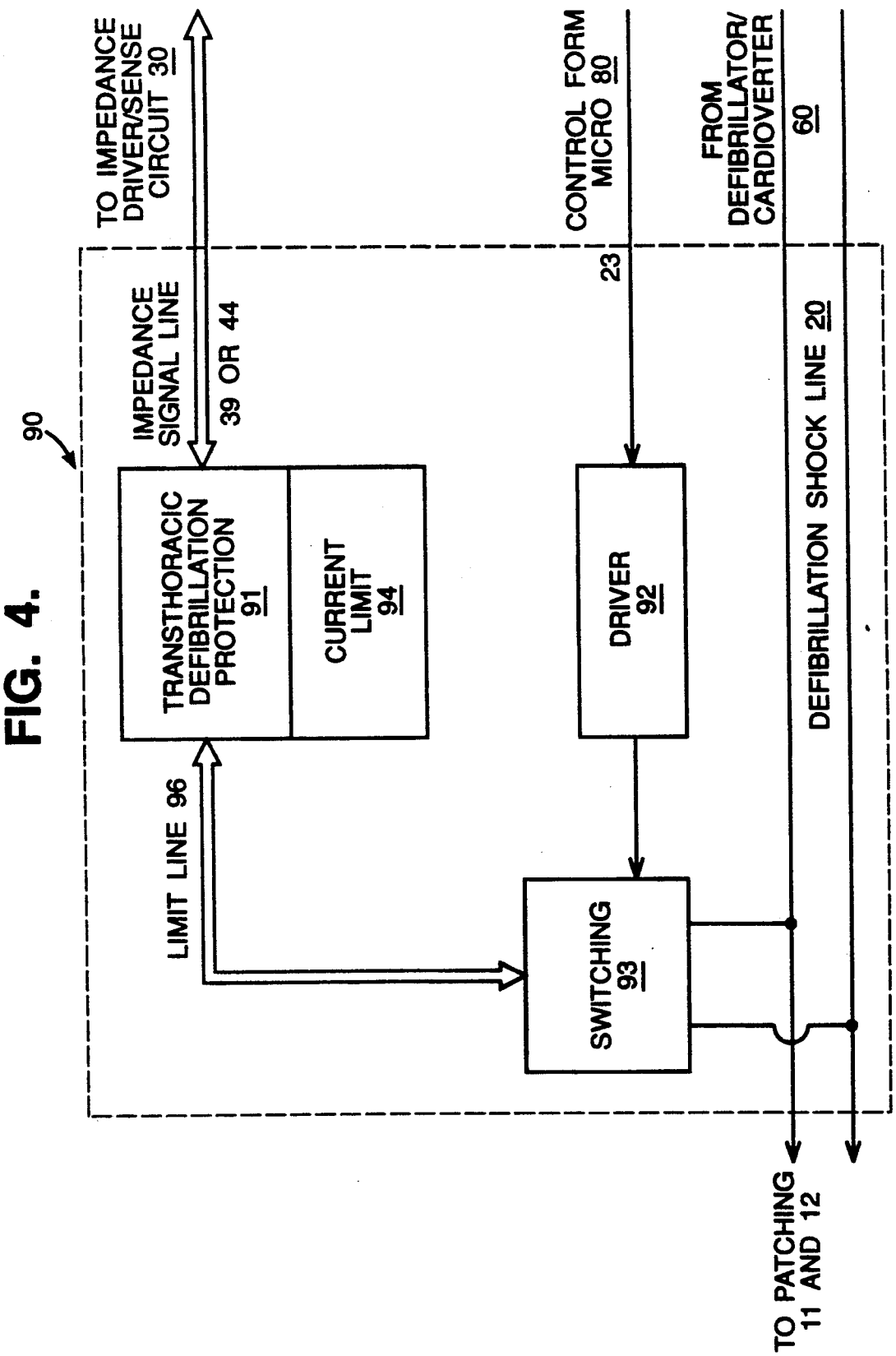
FIG. 4 illustrates a block diagram of a defibrillation protection circuit that may be utilized in the system of FIG. 1 for the protection of the impedance drive/sense circuit against damage that may be caused by high voltage defibrillation shocks delivered either from an implantable arrhythmia control system, or from an external transthoracic defibrillation system.

Referring to FIG. 4, a preferred embodiment of the defibrillation protection circuit 90 is shown. There are two aspects to the defibrillation protection circuit 90. Firstly, the impedance driver/sense circuit 30 (FIG. 1) must be protected against the large voltages coupled on to the defibrillator patches 11 and 12 (FIG. 1) during transthoracic defibrillation. This may take the form of voltage and/or current limiting to a level greater than the level on the impedance signal line 39 or 44, yet lower than that which the impedance driver/sense circuit 30 (FIG. 1) can tolerate. This is achieved in a transthoracic defibrillation protection circuit 91 and a current limit circuit 94. Secondly, the impedance driver/sense circuit 30 (FIG. 1) must be protected against the large voltages delivered from the defibrillator/cardioverter 60 (FIG. 1) to the patches 11 and 12 (FIG. 1) during defibrillation or cardioversion therapy from the implantable arrhythmia control system 10 (FIG. 1). For this, a switching circuit 93 must isolate the impedance driver/sense circuit 30 (FIG. 1) from defibrillation shock line 20.

In the preferred embodiment, a control signal 23 from microprocessor 80 (FIG. 1) activates a switching driver 92 to drive a switching circuit 93 via line 97 to isolate a line 96 from the defibrillation shock line 20. The line 96 from switching circuit 93 passes through the transthoracic defibrillation protection circuit 91 and, depending on the configuration of the impedance driver/sense circuit 30 (FIG. 1), communicates either along line 39 or line 44 with the impedance driver/sense circuit 30 (FIG. 1). The control signal 23 from microprocessor 80 (FIG. 1) will be activated immediately prior to the delivery of any defibrillation or cardioversion shock from defibrillator/cardioverter 60 (FIG. 1) along defibrillation shock line 20, past the switching circuit 93, to the patches 11 and 12 (FIG. 1) and ventricles 13 and 14 (FIG. 1). Immediately following shock delivery, the control signal 23 from microprocessor 80 deactivates the driver 92 and hence switching circuit 93, to allow re-connection between the patches 11 and 12 (FIG. 1) and the impedance driver/sense circuit 30 (FIG. 1), via the current limiting circuit 94 and the transthoracic defibrillation protection circuitry 91.

Figure 5:
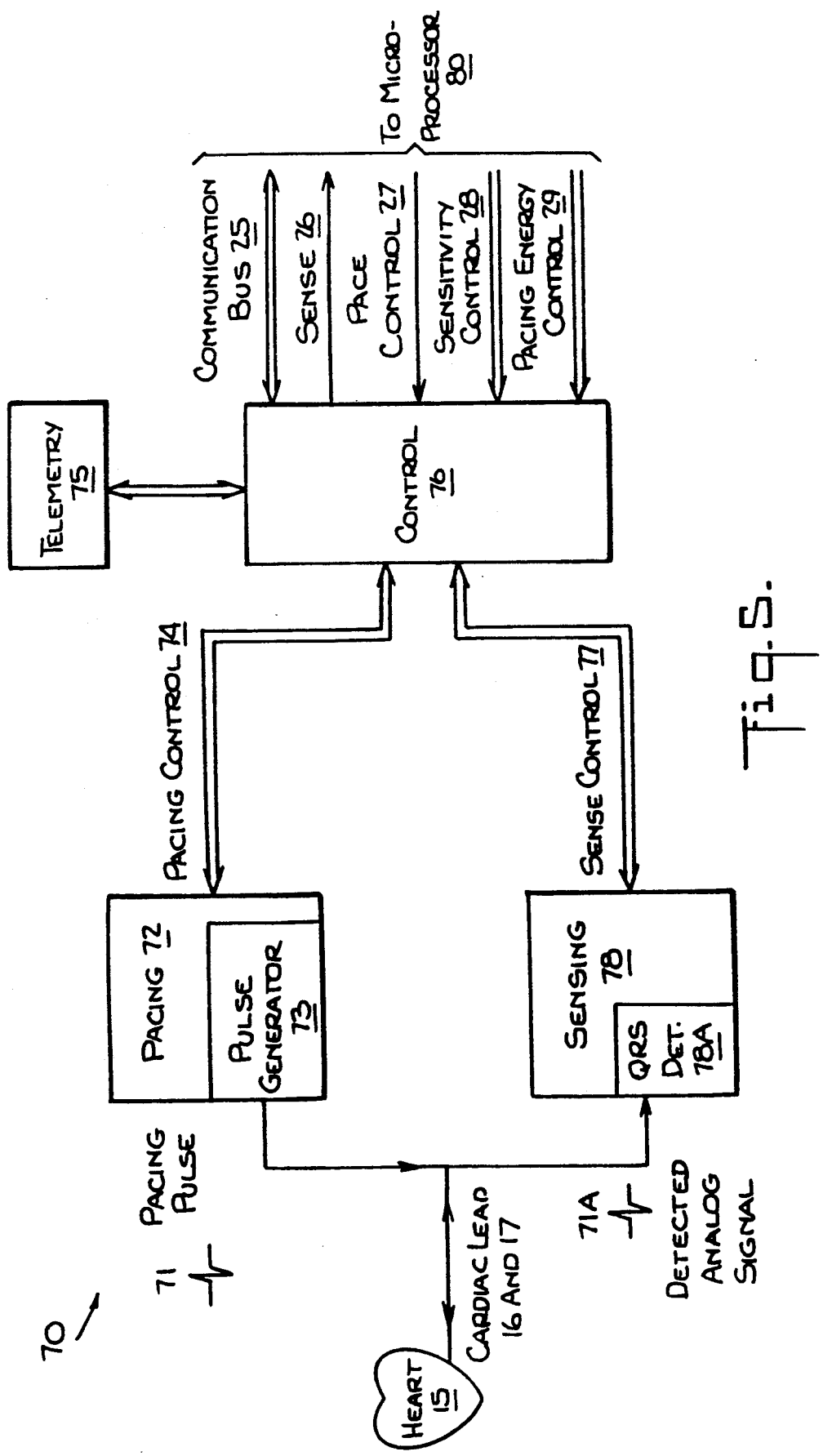
FIG. 5 illustrates a block diagram of a pacemaker circuit which may be incorporated within the implantable arrhythmia control system of FIG. 1.

Referring to FIG. 5, pacemaker 70 is shown in block diagram form. Pacemaker 70 comprises a pacing circuit 72 which includes a pacing pulse generator 73. Pacemaker 70 further includes a sensing circuit 78 and a telemetry circuit 75. In addition, there is a control block 76 which includes an interface to microprocessor 80 (FIG. 1).

In operation, sensing circuit 78 detects analog signals 71A from the heart 15 in an internal QRS detector 78A and converts the detected signals to digital signals. Furthermore, sensing circuit 78 receives an input sense control signal, which establishes the sensitivity of the detection circuits in sensing circuit 78, by way of a sense control bus 77 from control block 76. A change in this sensitivity will affect the voltage deviation required at the sensing electrode for a sense to be registered.

Pacing circuit 72 also receives inputs from control block 76, including a pace control and a pacing energy control, by way of pacing control bus 74, which carries the signals that arrive at control block 76 on pace control line 27 and pacing energy control bus 29. The pace control determines the type of pacing to occur, while the magnitude of the pulse energy is determined by the pacing energy control. Pacing circuit 72 causes pulse generator 73 to generate any required pacing pulses 71, which are delivered to the patient's heart 15 by means of cardiac leads 16 and 17.

Telemetry circuit 75 provides a bidirectional link between control block 76 of pacemaker 70 and an external device such as a programmer. It allows data such as the operating parameters to be read from or altered in the implanted arrhythmia control system 10 (FIG. 1).

Signals received from telemetry circuit 75 permit an external programmer (not shown) to change the operating parameters of pacemaker 70 by supplying appropriate signals to control block 76. Communications bus 25 serves to provide signals indicative of such control to microprocessor 80 (FIG. 1). Thus, it is also possible for an external programmer to control operation of defibrillator 60 (FIG. 1) by means of signals provided to the microprocessor 80.

Appropriate telemetry commands may cause telemetry circuit 75 to transmit data to the external programmer. Data stored is read out, by microprocessor 80 (FIG. 1) on to communications bus 25, through control block 76 in pacemaker 70, and into telemetry circuit 75 for transmission to the external programmer by a transmitter in telemetry circuit 75.

Figure 6:
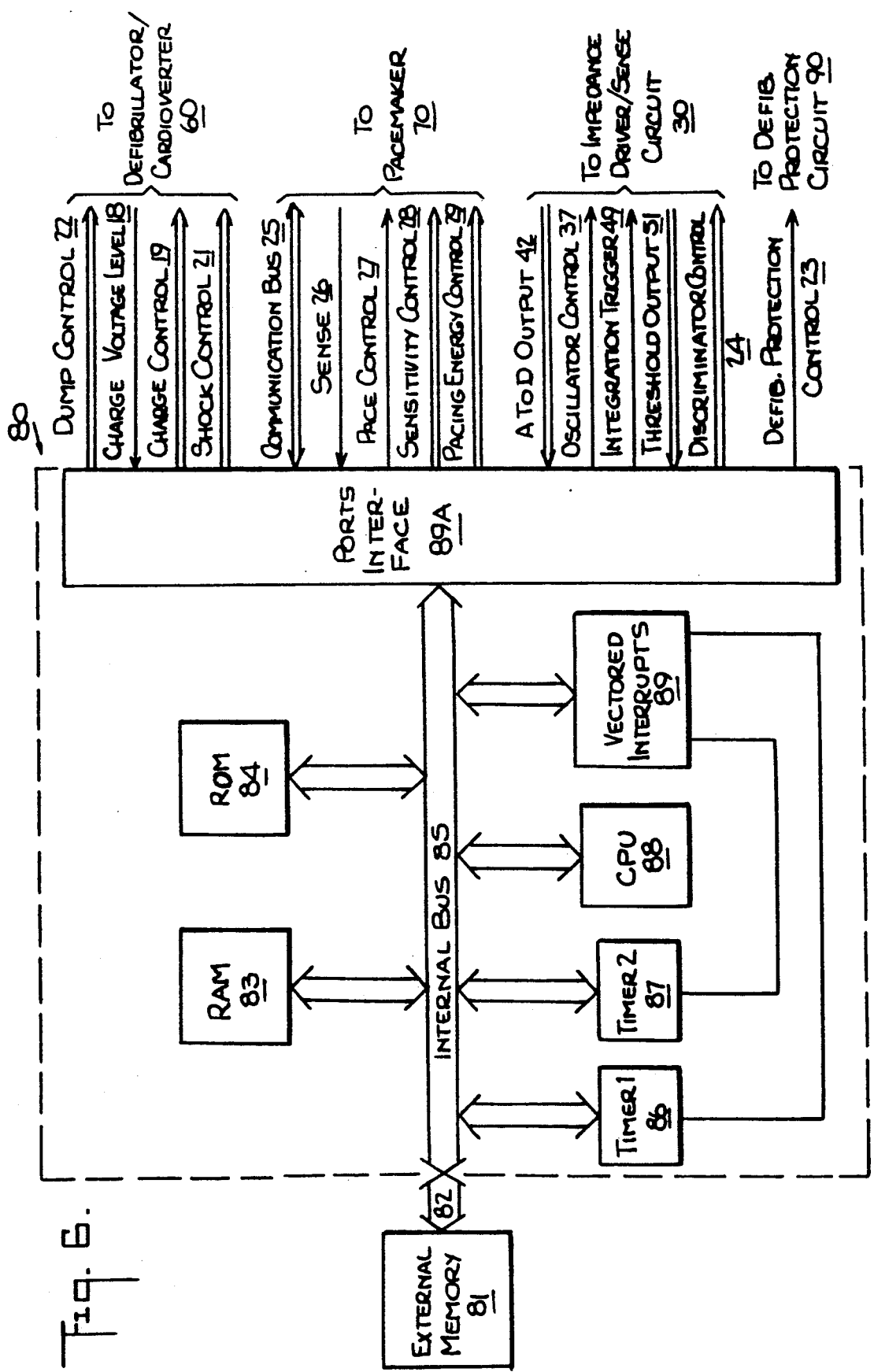
FIG. 6 illustrates a block diagram of a microprocessor which may be incorporated within the implantable arrhythmia control system of FIG. 1.

Referring to FIG. 6, the microprocessor 80 comprises two 16-bit timers 86 and 87, a central processing unit or CPU 88, a vectored interrupts block 89, a random access memory or RAM 83, a read only memory or ROM 84, a ports interface 89A, and an internal communications bus 85. RAM 83 acts as a scratch pad and active memory during execution of the various programs stored in ROM 84 and used by microprocessor 80. These programs include system supervisory programs, detection algorithms for detecting various arrhythmias both from the ECG and from impedance signals, and programming, as well as storage programs for storing, in external memory 81 via communications bus 82, data concerning the functioning of the arrhythmia control system 10 module, as well as the electrogram provided by cardiac leads 16 and 17 (FIG. 1) and the change in impedance from patches 11 and 12 (FIG. 1). Timers 86 and 87 and associated control software implement some timing functions required by microprocessor 80 without resorting entirely to software, thus reducing computational loads on and power dissipation by CPU 88.

Microprocessor 80 receives various status and/or control inputs from pacemaker 70 (FIG. 5), impedance driver/sense circuit 30 (FIG. 1) and defibrillator 60 (FIG. 1). During normal pacer operations, the output signal from pacemaker 70 (FIG. 5) is a sense signal on sense line 26 which is used by microprocessor 80 to perform operations such as arrhythmia detection. In addition, microprocessor 80 receives threshold output signal 51 and A/D output signal 42 from the impedance driver/sense circuit 30 (FIG. 1), also for arrhythmia detection and/or confirmation.

Microprocessor 80 produces outputs such as the pace control on pace control line 27 which determines the type of pacing to take place. Other pacemaker control outputs generated by microprocessor 80 include a pacing energy control signal on pacing energy control bus 29, which determines the magnitude of the pulse energy, and a sensitivity control signal on sensitivity control bus 28, which determines the sensitivity setting of the sensing circuit. Microprocessor 80 provides outputs to the impedance driver/sense circuit (FIG. 1) to control the driver oscillator 31 (FIGS. 2 and 3), the integrator (not shown) via line 49, if that is incorporated in the impedance driver/sense circuit, the amplitude discriminator 36 (FIGS. 2 and 3) and the threshold circuit 50 (FIGS. 2 and 3). In addition, microprocessor 80 provides a control output 23 to the defibrillation protection circuit 90 (FIG. 1).

Microprocessor 80 provides to defibrillator 60 (FIG. 1) a shock control signal on shock control line 21 which indicates that a shock is to be delivered to the patient, a dump control signal on dump control line 22 which indicates that a shock is to be dumped at an internal load within the defibrillator 60 (FIG. 1), and a charge control signal on charge control bus 19 which determines the voltage level of the shock to be delivered. Charge voltage level line 18 provides a digital signal representative of charged voltage from an analog to digital converter within defibrillator 80 (FIG. 1), thus providing a feed back loop which assures that a shock of proper energy level is delivered by defibrillator 80 (FIG. 1).

Figure 7:
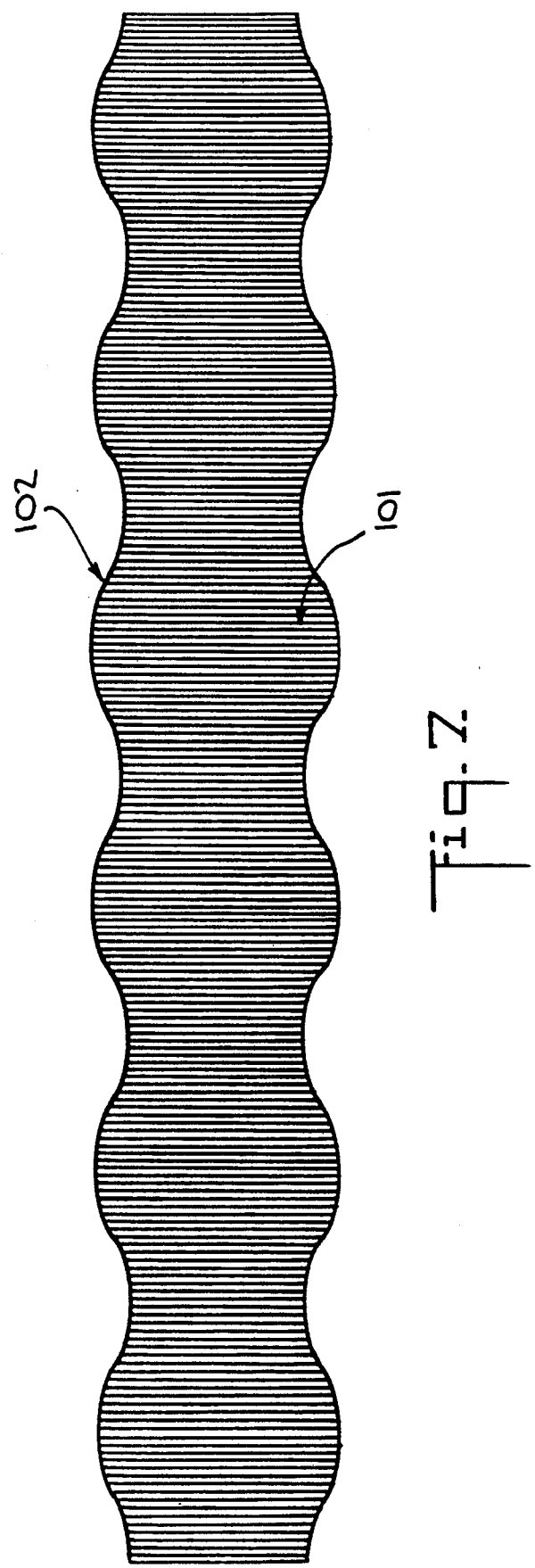
FIG. 7 illustrates a pictorial representation of the concept of amplitude modulation.

Referring now to FIG. 7, a schematic diagram representing signal amplitude modulation is shown. In this case a sinusoidal wave 101, oscillating at a high frequency in the range of 100 KHz, is modulated in amplitude such that an envelope 102 can be observed. This envelope 102 has an apparent oscillation frequency in the vicinity of only 2 Hz. Due to the comparatively rapid sine wave 101 oscillations, the envelope 102 is, for all intents and purposes, continuous as shown. In the demodulator 34 of FIGS. 2 and 3, the high frequency sine wave 101 is electronically removed from a modulated signal such as the one shown in FIG. 7, leaving the residual envelope 102 remaining. The envelope 102 becomes the demodulator output signal 41 (FIGS. 2 and 3) for either integration, if incorporated, or amplitude discrimination in the amplitude discriminator 36 (FIGS. 2 and 3) within the impedance driver/sense circuit 30 (FIG. 1).

Referring now to FIG. 8A there is shown an example of a trace 110 showing the change in amplitude of the modulations of a 100 KHz sine wave in response to the induction of fibrillation of the ventricles 13 and 14 (FIG. 1) of the heart 15. A corresponding concurrent electrogram trace 111 is shown in FIG. 8B. It is to be understood that, during ventricular fibrillation, there is little mechanical movement of the ventricles 13 and 14 (FIG. 1) of the heart 15 as compared with their normal rhythmic contractions. The example of FIG. 8A is a direct copy of a recording made with a device similar to the impedance driver/sense circuit 30 (FIG. 2), except that the output for recording was taken from the demodulator output 41 (FIG. 2). Trace 111 of FIG. 8B shows the corresponding electrogram before the induction of ventricular fibrillation (VF) at 112, during the induction of VF at 113, and during VF at 114. Note that during the induction of VF, the impedance amplitude modulated signal 116 of FIG. 8A drops rapidly in amplitude from that existing before the induction of VF at 115, to become very low amplitude modulations, as shown at 117.

Referring now to FIG. 9, there is illustrated an example of a trace 120 which shows the change in amplitude of the modulations of a pulsed 50 ms wide square wave with a repetition rate of 20 Hz, in response to the induction of tachycardia of the ventricles 13 and 14 (FIG. 1) of the heart 15, and a corresponding electrogram trace 121. Note that, during ventricular tachycardia, shown at 127, though there is little mechanical movement of the ventricles 13 and 14 (FIG. 1) of the heart 15 as compared with their normal rhythmic contractions, there is more movement than during ventricular fibrillation (which is shown at 117 of FIG. 8A).

The trace 120 is a direct copy of a recording made with a device similar to the impedance driver/sense circuit 30 (FIG. 2), except that the output for recording was taken from the demodulator output 41 (FIG. 2) and the oscillations from oscillator 31 (FIG. 2) were intermittent. Trace 121 shows, at 122, the corresponding electrogram before the induction of ventricular tachycardia (VT) and, at 124, during VT. The induction of VT, indicated at 123, cannot be clearly seen on the electrogram trace 121 because the large impedance amplitude signal 126 of trace 120 partially obscures it. This is not of concern for two reasons: 1) the implantable arrhythmia control system is required to detect the actual arrhythmia and 2) the induction is not physiological and would not occur in a patient. During the induction of VT, the impedance amplitude modulated signal 126 can be seen to be electrically saturated by the induction stimulus. This is a result of the induction technique employed and, as such, is neither physiological nor found in patients who may wear an implantable arrhythmia control system. The impedance amplitude modulated signal 120 can, however, be seen to decrease in amplitude substantially after the induction of VT, as shown at 127, as compared with the normal rhythm before the induction of VT, shown at 125.

Referring now to FIGS. 10A and 10B, together, there is an example of a series of traces, designated generally at 130, showing the change in amplitude of the impedance modulations of a 100 KHz sine wave in response to artificial pacing of the ventricles 13 and 14 (FIG. 1) of the heart, and a corresponding series of electrogram traces, designated generally at 131. The responses of the impedance amplitude modulated signal to four different pacing rates are compared with the amplitude modulated signal recorded during normal heart contractions. It needs to be understood that, as the heart rate is increased via artificial pacing, the filling time of the ventricles 13 and 14 (FIG. 1) is reduced, and as such, the haemodynamics of the heart 15 (FIG. 1) become increasingly more compromised. In addition, the examples of FIGS. 10A and 10B show responses to ventricular pacing in an animal which had a resting heart rate of 130 beats per minute (bpm). It therefore needs to be understood that the pacing rates of up to 240 pulses per minute (ppm) are not considered to be excessive.

The example of FIG. 10A is a direct copy of a recording made with a device similar to the impedance driver/sense circuit 30 (FIG. 2), except that the output for recording was taken from the demodulator output 41 (FIG. 2). Traces 131 of FIG. 10B show electrograms corresponding to the impedance amplitude modulated signals (Delta Z) of FIG. 10A. Trace 132 shows a section of recording of the Delta Z response during normal sinus rhythm, corresponding to normal haemodynamic status. Trace 133 shows the corresponding electrogram. Trace 134 shows a section of recording of the Delta Z response during ventricular pacing at 150 ppm. Note the diminished amplitude of the Delta Z signal corresponding to compromised haemodynamics. Trace 135 shows the corresponding electrogram to trace 134. Similarly, traces 136, 138 and 140 show sections of recordings of the Delta Z response to ventricular pacing at rates of 180, 210 and 240 ppm, respectively. Note the continued diminution of Delta Z amplitude corresponding both to increased pacing rate and to further haemodynamic compromise. Traces 137, 139 and 141 are the electrograms corresponding to traces 136, 138 and 140, respectively.

It will be apparent from the foregoing description that the present invention provides a device capable of measuring haemodynamic compromise in both ventricles of the patient's heart by determining the changes in normal variations of the transcardiac impedance between defibrillator patches placed on the outer surface of the patient's heart. In addition, the invention provides a device capable of classifying and detecting tachyarrhythmias according to discrete levels of haemodynamic compromise sensed by the device. Further, the invention provides a safe, reliable device capable of delivering appropriate antitachyarrhythmia therapy according to the discrete level of haemodynamic compromise sensed by the device.

Although the invention has been described with reference to particular embodiments, it is to be understood that such embodiments are merely illustrative of the application of the principles of the invention. Hence, numerous modifications may be made therein, and other arrangements may be devised, without departing from the true spirit and scope of the invention. For example, the invention may be used in external or internal medical devices, and the number of patches may also be three or even a higher number. Additionally, although two electrodes for impedance measurements and for defibrillation/cardioversion therapy are described in the preferred embodiment, the device and method as disclosed are not limited to this number of electrodes. For practical purposes, there may be three or more of such electrodes used in the device.

What is claimed is:

1. Apparatus for measuring the haemodynamic condition of a patient's heart, comprising:
   at least two cardioversion/defibrillation electrodes adapted to be positioned on the outer surface of the ventricles of the patient's heart generally across the short axis of said ventricles whereby at least the major portion of one of said electrodes is positioned on the left ventricular free wall;
   means coupled to said electrodes for sensing normal variations in the transcardiac impedance between said electrodes and determining the magnitude thereof;
   means for determining changes in the magnitude of the pulsations of said normal variations of said transcardiac impedance; and
   means responsive to said pulsation magnitude changes in normal variations of said transcardiac impedance for providing signals indicative of changes in the haemodynamic condition of the patient's heart.

2. Apparatus according to claim 1, further including heart malfunction treatment means responsive to said signals for selectively providing or not providing therapy to the patient's heart based on levels of haemodynamic compromise represented by said signals.

3. Apparatus according to claim 1, further including heart malfunction treatment means responsive to said signals for selectively providing one of a plurality of different therapies to the patient's heart, and wherein the therapy selected corresponds to a level of haemodynamic compromise represented by said signals.

4. Apparatus according to claim 2, wherein said signals comprise first signals representative of haemodynamic function, wherein said apparatus is implantable in the patient and further includes at least two additional electrodes adapted to be positioned within the patient's heart and means coupled to said additional electrodes for sensing an electrical function in the patient's heart and providing second signals representative of said electrical function, and wherein said heart malfunction treatment means is responsive both to said first signals and to said second signals in selectively providing or not providing therapy to the patient's heart.

5. Apparatus according to claim 3, wherein said signals comprise first signals representative of haemodynamic function, wherein said apparatus is implantable in the patient and further includes at least two additional electrodes adapted to be positioned within the patient's heart and means coupled to said additional electrodes for sensing an electrical function in the patient's heart and providing second signals representative of said electrical function, and wherein said heart malfunction treatment means is responsive both to said first signals and to said second signals in selectively providing one of said plurality of different therapies to the patient's heart.

6. Apparatus according to claim 4, wherein said at least two outer surface electrodes comprise defibrillation patches, and wherein said heart malfunction treatment means includes means for providing at least bradycardia support pacing therapy, antitachycardia pacing therapy and cardioversion/defibrillation therapy.

7. Apparatus according to claim 5, wherein said at least two outer surface electrodes comprise defibrillation patches, and wherein said heart malfunction treatment means includes means for providing at least bradycardia support pacing therapy, antitachycardia pacing therapy and cardioversion/defibrillation therapy.

8. Apparatus according to any one of claims 1-7, wherein said means coupled to said at least two outer surface electrodes for sensing normal variations in the transcardiac impedance between said electrodes includes a driver signal source circuit means for generating a non-polarization sub-threshold signal that is applied to said electrodes, and a sensed signal circuit means for sensing different amplitudes of modulation in said sensed signal due to variations in transcardiac impedance between said electrodes.

9. Apparatus according to claim 8, wherein said driver signal source circuit means generates a constant current output signal that is coupled to said first and second electrodes.

10. Apparatus according to claim 8, wherein said driver signal source circuit means generates a constant voltage output signal that is coupled to said at least two outer surface electrodes.

11. Apparatus according to claim 8, further including defibrillation protection means connected between said means for sensing normal variations in said transcardiac impedance and said at least two outer surface electrodes for selectively decoupling said means from said electrodes during any application of defibrillation therapy to the patient's heart.

12. Apparatus according to claim 7, wherein said means coupled to said at least two outer surface electrodes for sensing normal variations in the transcardiac impedance between said electrodes includes a driver signal source circuit means for generating a nonpolarizing sub-threshold signal that is applied to said electrodes, and a sensed signal circuit means for sensing different amplitudes of modulation in said sensed signal due to variations in transcardiac impedance between said electrodes, said sensed signal circuit means further including demodulating means for both demodulating said sensed signal and filtering out any DC offset in said signal, and discriminator means for determining the amplitude of each cycle of said demodulated signal and either averaging the amplitudes of a predetermined number of such cycles or detecting cycle amplitudes that cross predetermined threshold boundaries.

13. Apparatus according to claim 7, wherein said means coupled to said at least two outer surface electrodes for sensing normal variations in the transcardiac impedance between said, electrodes includes a driver signal source circuit means for generating a nonpolarizing sub-threshold signal that is applied to said electrodes, and a sensed signal circuit means for sensing different amplitudes of modulation in said sensed signal due to variations in transcardiac impedance between said electrodes, said sensed signal circuit means further including demodulating means for both demodulating said sensed signal and filtering out any DC offset in said signal, and integration means coupled to said demodulating means for integrating said demodulated signal, whereby said integrated signal represents electrical energy and changes in magnitude of such electrical energy represent changes in the level of haemodynamic compromise.

14. Apparatus according to claim 12, wherein said means for providing signals corresponding to changes in the haemodynamic condition of the patient's heart includes a digital microprocessor and an external memory coupled thereto, said external memory including a plurality of windows stored therein each of which corresponds to a different heart malfunction, treatment therapy, wherein said sensed signal circuit means includes analog to digital converter means coupled to both said discriminator means and said microprocessor for receiving output analog signals from said discriminator means, converting said analog signals to digital signals and passing said digital signals on to said microprocessor, and wherein said microprocessor maps said digital signals against said windows to determine the appropriate therapy, if any, to be delivered to the patient's heart.

15. Apparatus according to claim 13, wherein said means for providing signals corresponding to changes in the haemodynamic condition of the patient's heart includes a digital microprocessor and an external memory coupled thereto, said external memory including a plurality of windows stored therein each of which corresponds to a different heart malfunction treatment therapy, wherein said sensed signal circuit means includes analog to digital converter means coupled to both said integrator means and said microprocessor for receiving output analog signals from said integrator means, converting said analog signals to digital signals and passing said digital signals on to said microprocessor, and wherein said microprocessor maps said digital signals against said windows to determine the appropriate therapy, if any, to be delivered to the patient's heart.

16. A method of measuring the haemodynamic condition of a patient's heart, comprising:
   positioning at least two cardioversion/defibrillation electrodes on the outer surface of the ventricles of the patient's heart generally across the short axis of said ventricles whereby at least the major portion one of said electrodes is positioned on the left ventricular free wall;
   sensing normal variations in the transcardiac impedance between said electrodes and determining the magnitude thereof;
   determining changes in the magnitude of pulsations of said normal variations of said transcardiac impedance; and,
   providing signals indicative of changes in the haemodynamic condition of the patient's heart responsive to said pulsation magnitude changes in normal variations of said transcardiac impedance.

17. A method according to claim 16, further including the step of selectively providing or not providing therapy to the patient's heart based on the levels of haemodynamic compromise represented by said signals.

18. A method according to claim 16, further including the step of selectively providing one of a plurality of therapies to the patient's heart, and wherein the therapy selected corresponds to a predetermined level of haemodynamic compromise represented by said signals.

19. A method according to claim 17, wherein said signals comprise first signals representative of haemodynamic function, and further including the steps of positioning at least two additional electrodes within the patient's heart, sensing an electrical function in the patient's heart, and providing second signals representative of said electrical function, and wherein said step of selectively providing or not providing therapy to the patient's heart is based both on the level of haemodynamic compromise represented by said first signals and on the state of the electrical function represented by said second signals.

20. A method according to claim 18 wherein said signals comprise first signals representative of haemodynamic function, wherein said plurality of different therapies include at least bradycardia support pacing therapy, antitachycardia pacing therapy and defibrillation therapy, and further including the steps of positioning at least two additional electrodes within the patient's heart, sensing an electrical function in the patient's heart, and providing second signals representative of said electrical function, and wherein said step of selectively providing one of said plurality of different therapies to the patient's heart is based both on the level of haemodynamic compromise represented by said first signals and on the state of the electrical function represented by said second signals.

21. A method according to any one of claims 16-20, wherein said step of sensing normal variations in the transcardiac impedance between said electrodes includes the further steps of generating a non polarizing sub-threshold constant current signal, applying said signal to said first and second electrodes and sensing different amplitudes of modulation in said signal due to variations in transcardiac impedance between said electrodes.

22. A method according to any one of claims 16-20, wherein said step of sensing normal variations in the transcardiac impedance between said electrodes includes the further steps of generating a non-polarizing sub-threshold constant voltage signal, applying said signal to said at least two outer surface electrodes, and sensing different amplitudes of modulation in said signal due to variations in transcardiac impedance between said electrodes.

23. A method according to claim 21, including the further steps of demodulating said sensed signal, and filtering out any DC offset in said signal.

24. A method according to claim 23, including the further step of determining the amplitude of each cycle of said demodulated signal.

25. A method according to claim 23, including the further step of integrating said demodulated signal.

26. A method according to claim 24, including the further step of averaging the amplitudes of a predetermined number of said cycles.

27. A method according to claim 24, including the further step of detecting cycle amplitudes that cross predetermined threshold boundaries.

28. A method according to claim 22, including the further steps of demodulating said sensed signal, and filtering out any DC offset in said signal.

29. A method according to claim 28, including the further step of determining the amplitude of each cycle of said demodulated signal.

30. A method according to claim 28, including the further step of integrating said demodulated signal.

31. A method according to claim 29, including the further step of averaging the amplitudes of a predetermined number of said cycles.

32. A method according to claim 29, including the further step of detecting cycle amplitudes that cross predetermined threshold boundaries.

* * * * *